United States Patent
Elshihabi

(10) Patent No.: US 9,259,244 B2
(45) Date of Patent: Feb. 16, 2016

(54) SPINE STABILIZATION SYSTEM WITH SELF-CUTTING ROD

(71) Applicant: Said Elshihabi, Atlanta, GA (US)

(72) Inventor: Said Elshihabi, Atlanta, GA (US)

(*) Notice: Subject to any disclaimer, the term of this patent is extended or adjusted under 35 U.S.C. 154(b) by 0 days.

(21) Appl. No.: 14/537,686

(22) Filed: Nov. 10, 2014

(65) Prior Publication Data

US 2015/0066092 A1    Mar. 5, 2015

Related U.S. Application Data

(62) Division of application No. 13/455,615, filed on Apr. 25, 2012, now Pat. No. 8,882,806.

(60) Provisional application No. 61/478,596, filed on Apr. 25, 2011.

(51) Int. Cl.
*A61B 17/70* (2006.01)

(52) U.S. Cl.
CPC ........... *A61B 17/7002* (2013.01); *A61B 17/701* (2013.01); *A61B 17/7032* (2013.01); *A61B 17/7037* (2013.01)

(58) Field of Classification Search
CPC ............................. A61B 17/70; A61B 17/7002

USPC .......................... 606/246, 261, 264–267, 279
See application file for complete search history.

(56) References Cited

U.S. PATENT DOCUMENTS

| | | |
|---|---|---|
| 5,591,235 A | 1/1997 | Kuslich |
| 2007/0179343 A1 | 8/2007 | Shelokov |
| 2007/0191841 A1 | 8/2007 | Justis et al. |
| 2008/0319490 A1* | 12/2008 | Jackson ............ 606/308 |
| 2009/0048632 A1 | 2/2009 | Firkins |
| 2009/0163955 A1 | 6/2009 | Moumene |
| 2009/0222042 A1 | 9/2009 | Firkins |
| 2009/0326588 A1 | 12/2009 | Felix et al. |
| 2010/0063544 A1 | 3/2010 | Butler |
| 2010/0106192 A1 | 4/2010 | Barry |
| 2010/0106193 A1 | 4/2010 | Barry |
| 2010/0114167 A1 | 5/2010 | Wilcox et al. |

* cited by examiner

*Primary Examiner* — Pedro Philogene
*Assistant Examiner* — David C Comstock
(74) *Attorney, Agent, or Firm* — MH2 Technology Law Group, LLP

(57) ABSTRACT

A spine stabilization system is provided. The system utilizes a self-cutting rod having a sharp cutting edge that can be anchored to a patient's spine with pedicle screws. The system can be percutaneously delivered, low profile, and allow cutting of surrounding tissue rather than simply spreading the tissue apart during rod insertion.

4 Claims, 5 Drawing Sheets

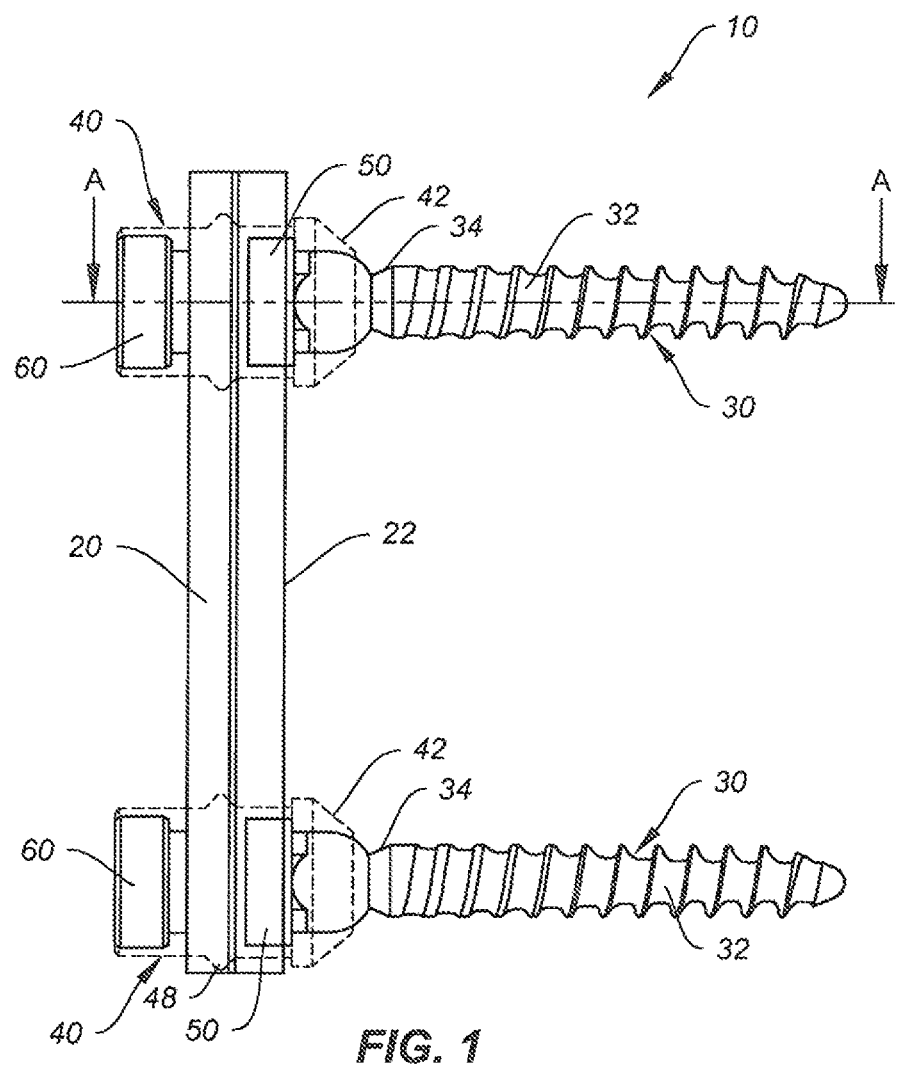
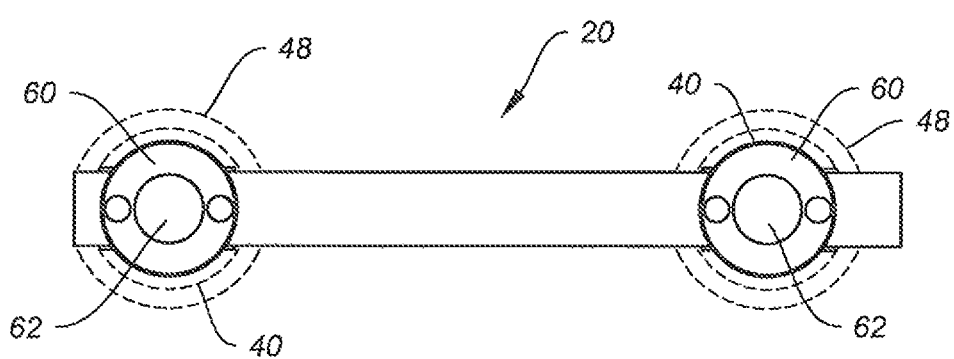

AMENDED FIG. 4B

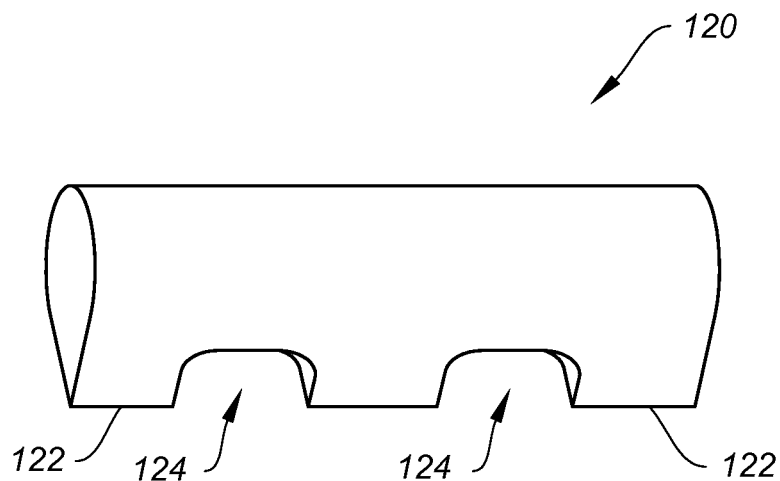
*AMENDED FIG. 8A*
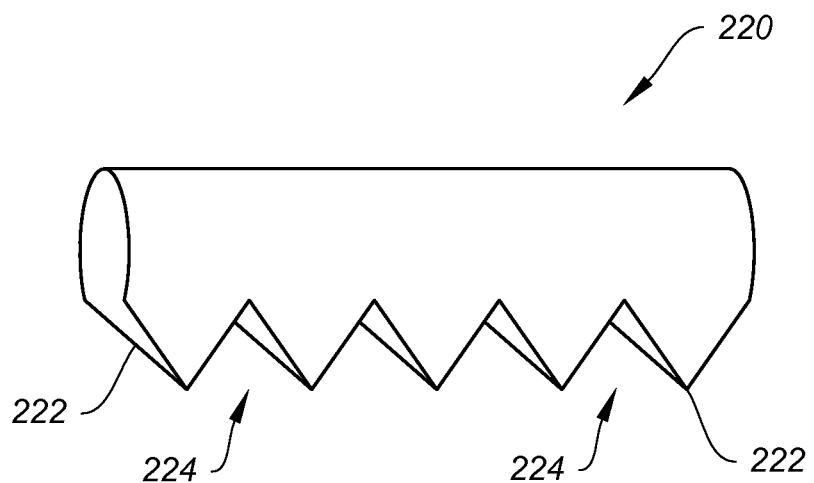
*FIG. 8B*

SPINE STABILIZATION SYSTEM WITH SELF-CUTTING ROD

CROSS-REFERENCE TO RELATED APPLICATIONS

This application is a divisional of U.S. patent application Ser. No. 13/455,615 filed Apr. 25, 2012 (now allowed), and which claims benefit of U.S. Provisional Application No. 61/478,596 filed Apr. 25, 2011, and entitled "Spine Stabilization System with Self-Cutting Rod," the contents of which are incorporated herein by reference in their entirety.

FIELD

The present invention relates to spine stabilization systems having a rod for spine stabilization that is anchored with fixation screws, and more particularly to a spine stabilization system utilizing a self-cutting rod that can be fixed to a patient's spine with pedicle screws.

BACKGROUND

Spinal correction surgery is used to correct spine deformities, disorders, or diseases, and otherwise stabilize the spine. Spinal correction surgery is sometimes needed to relieve pain or correct the alignment of a patient's spine. For example, spinal correction surgery is often used to treat spinal diseases, such as scoliosis and osteoarthritis, as well as degenerative disc diseases.

Pedicle screws are an integral part of most spinal correction surgeries. For example, a common surgery involves an internal fixation of the damaged or diseased vertebrae using a pedicle screw implant with a fixed link to a plate or a rod. A critical diameter for spinal surgery is thus the inner diameter of the pedicle of the vertebral body being treated. The inner diameter, however, can vary widely because it is directly related a person's height and the anatomy of each individual's cervical spine, thoracic and lumbar spine, and sacrum. Therefore, for a successful spinal surgery, the surgeon must be able to understand each patient's anatomical differences.

In most rod fixation systems, the pedicle screws are attached to a rod receiving head that is typically shaped like a tulip head for connecting to the rod. Although most systems provide a screw and rod receiving head combination that can articulate relative to one another, so that the tulip heads can align after the screws are inserted into the bone, it is nevertheless still difficult and time consuming to properly align a rigid rod into a pair of tulip heads. Compounding this problem is the surrounding tissue around the insertion area, which can be extremely tough to circumvent. The surgeon often has to exert a significant amount of force to spread apart the native tissue in order to properly seat the rod inside the tulip heads, thereby creating even more trauma to the injury site. With the additional challenges previously mentioned with proper pedicle screw insertion, there is a need for a better, more efficient rod fixation system for the spine.

Accordingly, it is desirable to provide a spinal fixation system that utilizes known techniques of rod stabilization with pedicle screws, but having the new feature of a self-cutting rod that has a cutting edge to quickly and easily insert in between the pedicle screws during implantation.

SUMMARY

The present disclosure provides a spine stabilization system utilizing a self-cutting rod that can be fixed to a patient's spine with pedicle screws. The system can be percutaneously delivered, low profile, and allow cutting of surrounding tissue rather than simply spreading the tissue apart during rod insertion.

In one embodiment, a spine stabilization system is provided. The spine stabilization system comprises fixation screws for anchorage to bone tissue. Each screw may comprise a shaft portion attached to a head portion at an articulating joint. The head portion may be configured to hold a rod therein. The system may also comprise a bushing having a saddle region or slot for receiving a rod, the bushing being configured to nest within the head portion. A rod having a cutting edge sufficiently sharp to tear through fascia and muscle tissue is also provided.

In another embodiment, a method for stabilizing a spine is provided. The method comprises providing a system having fixation screws for anchorage to bone tissue, each screw comprising a shaft portion attached to a head portion at an articulating joint, the head portion configured to hold a rod therein. The system may also comprise a bushing having a saddle region or slot for receiving a rod, the bushing being configured to nest within the head portion. A rod having a cutting edge sufficiently sharp to tear through fascia and muscle tissue is also provided. The method further includes the steps of inserting the fixation screws into bone tissue, and inserting the rod into the head portions of the fixation screws, wherein the step of inserting the rod comprises pressing the cutting edge of the rod through fascia and muscle tissue until the cutting edge of the rod is seated within the saddle region of the bushing.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 1 is a side view of an exemplary embodiment of a rod fixation system of the present disclosure.

FIG. 2 is a top-down view of the rod fixation system of FIG. 1.

FIG. 4B is an enlarged view of the encircled portion of the rod fixation system of FIG. 4A.

FIG. 8A is a perspective view of yet another exemplary Embodiment of a rod of the present disclosure.

FIG. 8B is a perspective view of event still another exemplary embodiment of a rod of the present disclosure.

DESCRIPTION OF THE EMBODIMENTS

The present disclosure provides a spine stabilization system utilizing a self-cutting rod that can be fixed to a patient's spine with pedicle screws, such as polyaxial screws. The system is configured as a rod fixation system that can be percutaneously delivered, low profile, and allow cutting through the surrounding tissue rather than simply spreading the tissue apart during rod insertion.

Figure 4A:
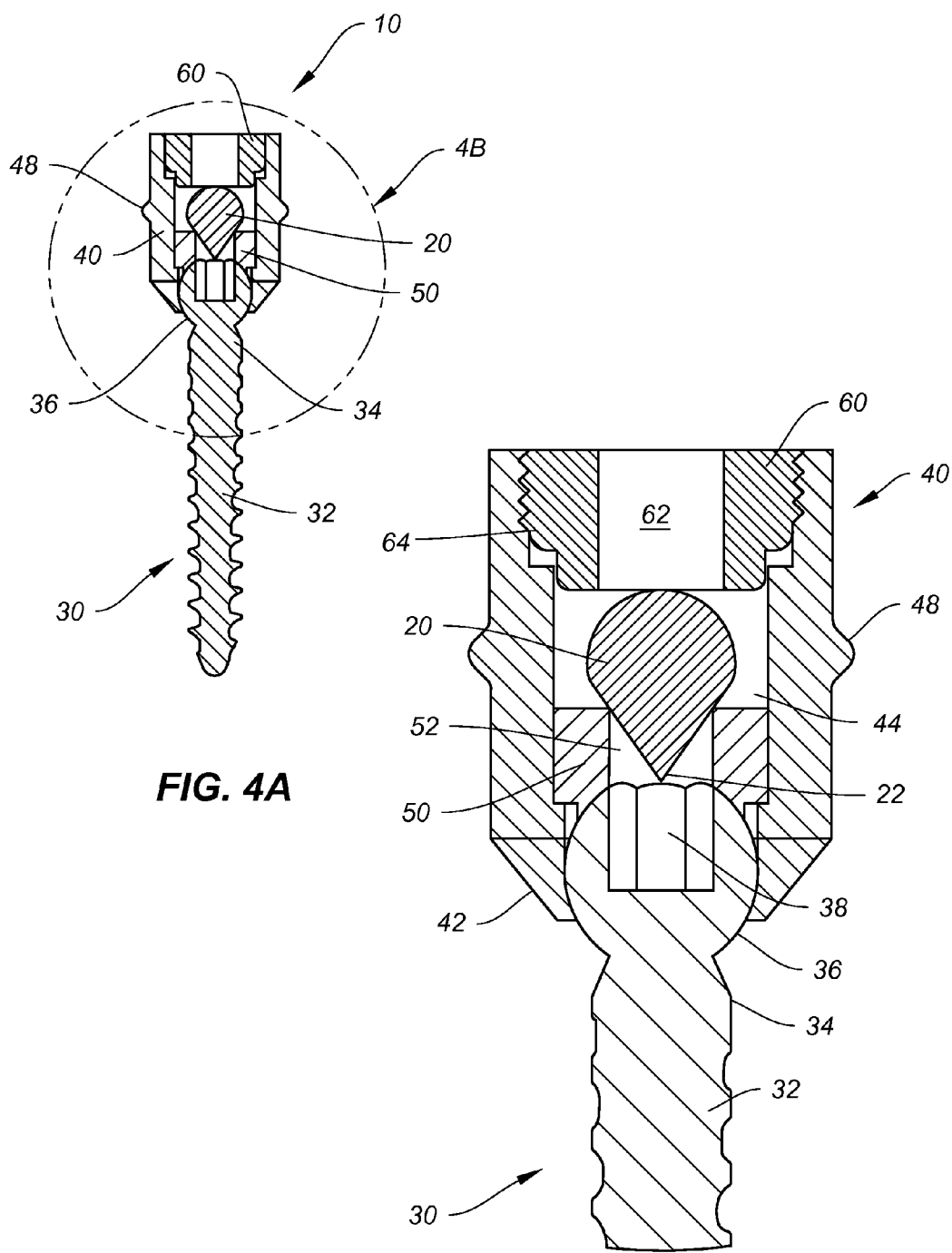
FIG. 4A is a cross-sectional view of the rod fixation system of FIG. 1 along lines A-A.

In FIG. 1, an exemplary embodiment of a spine stabilization system 10 of the present disclosure is shown. The spine stabilization system 10 may include a rod 20 for rigid fixation of a weakened, diseased or damaged vertebral segment of a patient's spine. The rod 20 may be anchored to the patient's spine with fixation elements such as pedicle screws 30. Pedicle screws 30 may be polyaxial for greater flexibility. Pedicle screws 30 may have a threaded shaft 32. In the embodiment shown, the threaded shaft 32 may be dual threaded, if so desired. The threaded shaft 32 may extend into a neck 34 that terminates into a rounded end or ball 36. A tool-engaging opening 38 may be provided on the ball 36 to allow the screw 30 to engage with insertion tools or drivers. For example, the opening 38 may be polygon-shaped (as shown in FIGS. 4A and 4B) such as for example, a hexagon-shaped opening.

Figure 3:
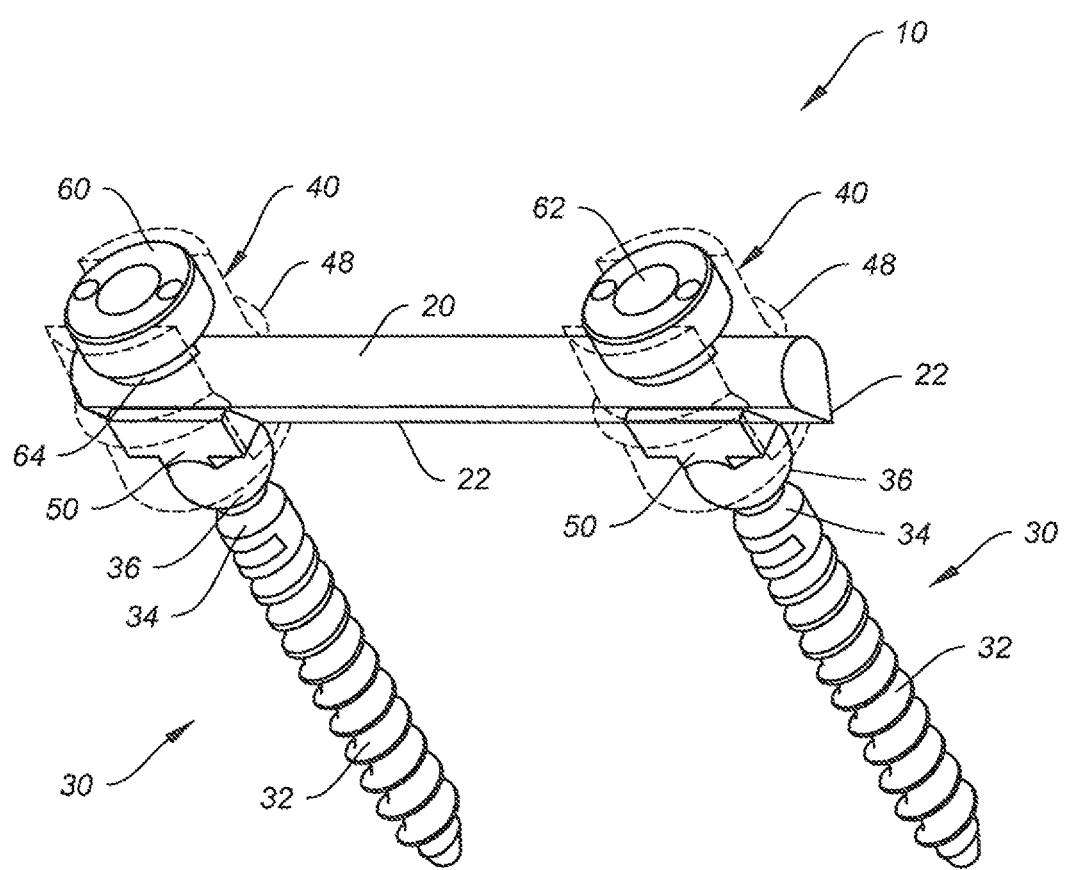
FIG. 3 is a perspective view of the rod fixation system of FIG. 1.

Referring now to FIG. 3, the ball 36 may be configured to cooperate with a head portion 40 of the screw 30. The head portion may be a generally tulip-shaped head. The head portion 40, or rod holder, of the screw 30 may have a hollow core 44 or opening, and a tapered end 42 at which the ball 36 of the screw 30 may rest. The ball 36 of the screw 30 and the tapered end 42 of the head portion 40 form a ball-and-socket type joint that allows some articulation of the head portion 40 relative to the shaft portion 32 of the screw 30. Within the hollow core 44 of the head portion 40 may be a bushing 50 that provides a slot or an open, saddle region 52 to hold and secure the rod 20 inside the head portion 40. The bushing 50 may be configured to nest within the head portion 40 and against the ball 36 of the screw 30, as shown in FIGS. 4A and 4B. The head portion 40 may also be provided with a flange 48 that encircles the exterior. This flange 48 may facilitate locating the head portion 40 during surgery by providing a visual cue, as well as serve as a convenient grip for handling the head portion 40.

As shown in FIG. 2, locking caps 60 may be provided to secure the rod 20 inside the head portion 40 and close off the hollow core 44. The locking caps 60 may comprise a tool bore 62 for receiving an insertion tool. The locking caps 60 may further comprise a threaded exterior 64 for threaded engagement with the head portion 40, as illustrated in detail in FIG. 4B. Of course, it is understood that threads are merely one example of an attachment mechanism. Other mechanisms may be equally employed, such as a snap-fit or press-fit arrangement between the locking cap 60 and the head portion 40.

The rod 20 of the present disclosure may include a cutting edge 22 sufficiently sharp enough to cut easily through surrounding tissues of the spine. The rod 20, in effect, is a cutting blade. And while the term "rod" generally refers to a cylindrical shaped object, as shown in FIGS. 3, 4A and 4B the rod 20 of the present embodiment may be teardrop-shaped, terminating at one end into its cutting edge 22. It is contemplated that the rod 20 may be suitable for transfacial and transmuscular insertion into the head portions 40 simply by exerting force onto the rod 20, whereby the cutting edge 22 will cut through the fascia and muscle easily and quickly. Unlike with conventional rods, the rods 20 of the present disclosure do not merely spread apart the surrounding tissue, but cut entirely through them when the rods 20 are lodged into place. It is believed that the clean, smooth cutting of the surrounding tissue in this manner not only saves a great deal of time during surgery, but also provides the additional benefit of disrupting less of the patient's natural tissue than with conventional spreading techniques. This localized cutting effect results in less pain post-surgery, and a faster and more complete healing of the surrounding tissue (i.e., compared to the healing time of a deep, clean cut versus a jagged edged, inconsistent cut).

In use, a surgeon would first implant the head portions 40, bushings 50 and pedicle screws 30 into the pedicles of the vertebrae to be rigidly fixed. As is commonly known in the art, the head portions 40, bushings 50 and pedicle screws 30 may be provided pre-assembled for convenience. After proper insertion of the pedicle screws 30, the surgeon may simply push down (by hand or with the assistance of a tool) on the rod 20 to seat the rod 20 inside the saddle region 52 of each of the two bushings 50 within the head portions 40. The cutting edge 22 of the rod 20 may be sufficiently sharp enough to cut through surrounding fascia and muscle without significant resistance, thereby allowing easy and fast insertion. When the self-cutting rod 20 has been properly seated, the locking caps 60 may be placed over the head portions 40 and the entire system 10 can be closed up. Due to the ability of the rod 20 to seat so closely to the ball 36 of the screw 30, the spine stabilization system 10 of the present disclosure offers a very low profile. Further, the entire system 10 may be percutaneously delivered.

Figures 5, 6, 7:
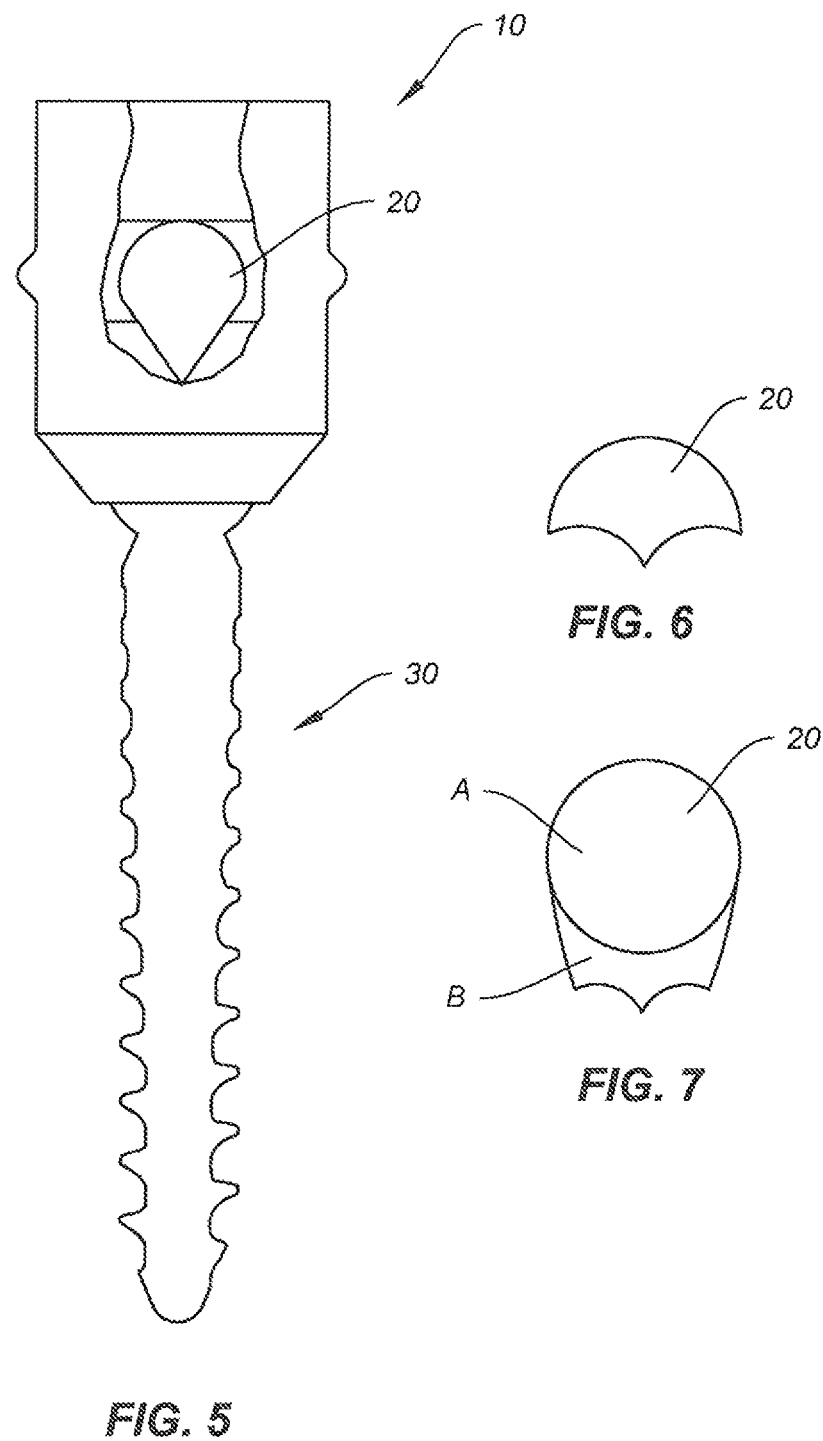
FIG. 5 is a partial cutaway end view of the rod fixation system of FIG. 1.
FIG. 6 is an end view of another exemplary embodiment of a rod of the present disclosure.
FIG. 7 is an end view of still another exemplary embodiment of a rod of the present disclosure.

In order to avoid any unintended and unnecessary tearing, scraping or damage to the tissues near the ends of the rod 20, the head portions 40 may be configured with a close-off end, as contemplated in the end view at FIG. 5 whereby a portion of the head portion 40 is removed to show the rod 20 inside the head portion 40. In other words, the head portion 40 itself (or in cooperation with the bushing 50 as a unit) forms a closed end that prevents the cutting edge 22 of the rod 20 from contacting adjacent tissue.

It is contemplated that the rod 20 may be formed of any suitable medical grade metal, such as titanium, titanium alloy, stainless steel, or cobalt chrome. The rod 20 may also be formed from a variety of other suitable biocompatible materials, either alone or in combination with one another, so long as the material provides enough rigidity for the rod 20 to serve as a spinal fixation implant. The rod 20 may be ABS injection molded plastic, polyetheretherketone (PEEK), polyethylene (PE), or ultra high molecular weight polyethylene (UHMWPE). If desired, the devices may be bioabsorbable or bioresorbable. In other embodiments, the rod 20 may be formed partially or wholly from a radiolucent material. For example, the rod 20 may be formed from a material blended with a radiopaque material, such as barium sulfate, to assist in the visualization of the rod 20 insertion process. In addition, radiopaque markers may be employed with the rod 20 as well as the head portion 40 for imaging possibilities. Additionally, the rod 20 may contain a coating having biological properties, such as with antibiotic, antimicrobial, blood coagulating, or bone growth promoting properties, as some examples. Other known biologically active agents may also be employed, as desired.

As previously mentioned, it is possible to combine rigid materials with other semi-rigid materials to form a composite rod 20. For instance, in one embodiment, the rod 20 may include a top side (i.e., rounded side) that is relatively softer than the cutting edge 22 (i.e., blade side). In addition, a soft coating may be applied to the top side for ease of handling, if so desired.

The cutting edge 22 may be integrally formed from rod 20. Alternatively, the cutting edge 22 may be a separate component that is attached to the rod 20 either permanently or semi-permanently. For example, the cutting edge 22 may be glued or mechanically attached to the rod 20 using screws, a press fit, an interference fit, and the like. The cutting edge 22 may thus be constructed from the same or different material as the rod 20. This allows for customization of the cutting edge 22, for example to provide a desired sharpness, width, and the like. The cutting edge 22 may also be formed from a variety of other suitable biocompatible materials, either alone or in combination with one another, so long as the material provides enough rigidity to serve as a cutting edge. The cutting edge 22 may be ABS injection molded plastic, PEEK, PE, or UHMWPE. If desired, some or all of the cutting edge 22 may be bioabsorbable or bioresorbable.

In other embodiments, the cutting edge may be formed partially or wholly from a radiolucent material. Additionally, the cutting edge 22 may contain a coating having biological properties, such as with antibiotic, antimicrobial, blood coagulating, or bone growth promoting properties, as some examples. Other known biologically active agents may also be employed, as desired. While the rod 20 of the present embodiment is shown as having a V-shaped cutting edge 22 from a side view, it is understood that other shapes may be employed, such as a W-shaped cutting edge, as shown in FIG. 6. Other shapes may also include waves, or jagged edges, serrations, or the like. In addition, it is possible to have a composite rod 20 comprising a rod-like portion A that attaches to a cutting-edge portion B, as shown in FIG. 7, for ease of manufacture. In one embodiment, the rod 20 (along with its cutting edge 22) may have a total diameter in the range of about 6.0 mm.

FIGS. 8A and 8B illustrate other embodiments of a cutting rod of the present disclosure. In FIG. 8A, the rod 120 shares similar features to the rod 20 previously described, with like elements sharing the same reference numeral following the prefix "1", while in FIG. 8B, the rod 220 shares similar features to the red 20 previously described, with like elements sharing the same reference numeral following the prefix "2". Rods 120, 220 may have intermittent cutting edges, or a discontinuous cutting edge when viewed as a whole. For example, rod 120 may be provided with a plurality of cutting edges 122, with non-cutting portions 124 separating the cutting edges 122 from each other. Likewise, rod 220 may also include a plurality of cutting edges 222, each cutting edge 222 being separated from the next by spaces or portions 224 that may not be specifically configured to cut through tissue. Of course, the cutting edges of the rods 120, 220 should be suitable for transfacial and transmuscular insertion into the screws 30 and configured to cut through the fascia and muscle easily and quickly, similar to the cutting edge 22 of rod 20.

The description of the invention is provided to enable any person skilled in the art to practice the various embodiments described herein. While the present invention has been particularly described with reference to the various figures and embodiments, it should be understood that these are for illustration purposes only and should not be taken as limiting the scope of the invention.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A method for stabilizing a spine comprising:
providing a spine stabilization system having fixation screws for anchorage to bone tissue, each screw comprising a shaft portion attached to a head portion at an articulating joint, the head portion configured to hold a rod therein, a bushing having a saddle region for receiving a rod, the bushing being configured to nest within the head portion of one of the fixation screws, and a self-cutting rod having a cutting edge sufficiently sharp to easily cut through fascia and muscle tissue, the self-cutting rod being configured as a cutting blade to cut through surrounding fascia or muscle tissue;
inserting the fixation screws into bone tissue; and
inserting the self-cutting rod into the head portions of the fixation screws;
wherein the step of inserting the self-cutting rod comprises pressing the cutting edge of the self-cutting rod through fascia and muscle tissue and into the saddle region of the bushing.

2. The method of claim 1, wherein the fixation screws are pedicle screws, and the bone tissue are pedicles.

3. The method of claim 1, further including the step of placing locking caps over the head portions.

4. The method of claim 1, wherein the system is assembled percutaneously.

* * * * *